United States Patent
Farer et al.

(10) Patent No.: US 6,656,483 B1
(45) Date of Patent: Dec. 2, 2003

(54) COSMETIC COMPOSITIONS CONTAINING POLYURETHANE

(75) Inventors: Alan Farer, Kinnelon, NJ (US); Christian J. Lee, Parsippany, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/714,715

(22) Filed: Nov. 16, 2000

(51) Int. Cl.[7] .......................... A61K 6/00; A61K 7/00; A61K 7/04

(52) U.S. Cl. ................................. 424/401; 424/61

(58) Field of Search .................. 424/401, 61

(56) References Cited

U.S. PATENT DOCUMENTS

| | | | |
|---|---|---|---|
| 3,301,760 A | 1/1967 | Jewel | 167/85 |
| 3,849,547 A | 11/1974 | Kalopissis | 424/61 |
| 4,891,213 A | 1/1990 | Gordon et al. | 424/61 |
| 4,996,284 A | 2/1991 | Mallavarapu | 528/92 |
| 5,066,484 A | 11/1991 | Castrogiovanni et al. | 424/61 |
| 5,093,108 A * | 3/1992 | Pappas et al. | 424/61 |
| 5,120,529 A | 6/1992 | Koch et al. | 424/61 |
| 5,145,670 A | 9/1992 | Castrogiovanni et al. | 424/61 |
| 5,225,185 A | 7/1993 | Castrogiovanni et al. | 424/61 |
| 5,227,155 A | 7/1993 | Castrogiovanni et al. | 424/61 |
| 5,290,543 A | 3/1994 | Ounanian et al. | 424/61 |
| 5,470,562 A | 11/1995 | Khamis | 424/61 |
| 5,478,551 A | 12/1995 | Busch, Jr. | 424/61 |
| 5,538,717 A | 7/1996 | La Poterie | 424/61 |
| 5,601,808 A | 2/1997 | Mellul et al. | 424/61 |
| 5,676,935 A | 10/1997 | Mellul et al. | 424/61 |
| 5,792,447 A | 8/1998 | Socci et al. | 424/61 |
| 5,807,540 A | 9/1998 | Junino et al. | 424/61 |
| 5,811,084 A | 9/1998 | Busch, Jr. et al. | 424/61 |
| 5,830,443 A | 11/1998 | Lee | 424/61 |
| 5,863,523 A | 1/1999 | Socci et al. | 424/61 |
| 5,882,636 A | 3/1999 | Mui et al. | 424/61 |
| 5,910,313 A | 6/1999 | Ramin et al. | 424/401 |
| 5,977,217 A | 11/1999 | Socci et al. | 524/35 |
| 5,989,575 A | 11/1999 | Razzano | 424/401 |
| 5,993,837 A | 11/1999 | Calello et al. | 424/401 |
| 6,080,413 A * | 6/2000 | Ellingson et al. | 424/401 |
| 6,123,931 A | 9/2000 | Ellingson et al. | 424/61 |

* cited by examiner

*Primary Examiner*—Thurman K. Page
*Assistant Examiner*—S. Howard
(74) *Attorney, Agent, or Firm*—Rupa Sen; Anthony M. Santini

(57) ABSTRACT

There is provided a cosmetic composition, preferably in the form of a nail polish, comprising a primary film former, one or more high-molecular weight polyurethanes, and, optionally, one or more arylsulfonamide epoxy resins.

21 Claims, No Drawings

COSMETIC COMPOSITIONS CONTAINING POLYURETHANE

BACKGROUND OF THE INVENTION

1. Field of the Invention

The present invention relates generally to cosmetic compositions. More particularly, the present invention relates to cosmetic compositions with film-forming agents for application to the skin and nails.

2. Description of the Prior Art

Desirable cosmetic characteristics of film-forming cosmetic compositions include: good application, the production of a uniform film of excellent sheen or gloss, rapid drying time, good adhesion, a certain amount of flexibility, and good film strength to avoid cracking and flaking of the film. Moreover, an often overlooked, but desired, characteristic is the absence of irritation of the skin, hair, and/or nails upon which the film-forming cosmetic composition is applied.

To achieve the above-identified characteristics, film-forming cosmetic compositions conventionally have a mixture of film forming agents. Typically, cellulose-based film formers, in particular, nitrocellulose or cellulose acetate butyrate, are used as "primary" film formers. Often, the primary film formers are combined with one or more "secondary" film formers, which increase the film-forming ability of the primary film former and improve the sheen and adhesion of the resulting films. Secondary film formers known in the art include alkyd resins, polyester resins, acrylic resins, low molecular weight polyurethane resins, polyamide resins, vinyl resins, arylsulfonamide aldehyde resins, and arylsulfonamide epoxy resins.

For example, U.S. Pat. No. 5,676,935 to Mellul et al. discloses that nitrocellulose, arylsulphonamide-epoxy resin, and polyurethane have been used as film-forming materials. However, polyurethanes presently used in the art are difficult to stabilize in pigmented cosmetic compositions. Generally, combining polyurethane resins and pigments within a single cosmetic composition results in the pigments falling out of the suspension, which is clearly undesirable.

U.S. Pat. No. 6,080,413 to Ellingson et al. is directed to polyurethane nail polish compositions that have from about 0.1% to about 40% by weight of a water-insoluble, film-forming polyurethane, and a carrier having a liquid diluent. The diluent has water, and one or more volatile organic solvents.

U.S. Pat. No. 6,123,931 also to Ellingson et al. is directed to polyurethane and polyacryl nail polish compositions. These compositions have from about 0.1% to about 40% by weight of a water-insoluble, film-forming polymer, water, and one or more volatile organic solvents. However, the polymer is one or more polyacryls, polymethacryls, polyurethane-polyacryl mixtures, polyurethane-polymethacryl mixtures, urethane-acryl copolymers, and mixtures thereof.

Notwithstanding the foregoing, it has been unexpectedly discovered that a cosmetic composition, particularly a nail enamel composition, including a cellulose-based primary film forming agent, in combination with one or more high molecular weight polyurethane resins as a secondary film forming and plasticizing agent, and, optionally, one or more epoxy resins, results in increased adhesion of the cosmetic composition onto the nail, superior flexibility (displacement), durability, film strength, and no significant loss of gloss over time.

Moreover, unlike conventional nail enamel compositions where the pigmented nail enamel coating transfers coating if the nails are rubbed onto, for example, a paper napkin, notwithstanding that the initial drying time (10 to 60 minutes) has passed and the nails appear perceptively dry, the nail enamel coating of the present composition is significantly more transfer resistant once the nails are perceptively dry.

SUMMARY OF THE INVENTION

It is an object of the present invention to provide a cosmetic composition with a combination of film-forming agents for application to the skin and nails.

It is another objective of the present invention to provide such a cosmetic composition having improved gloss, wear-resistance, adhesion, and flexibility and is more transfer resistant in less time.

These and other objects of the present invention are achieved by a cosmetic composition, preferably in the form of a nail polish, comprising a ceilulose-based primary film former, one or more high molecular weight polyurethanes, and, optionally, one or more arylsulfonamide epoxy resins.

DETAILED DESCRIPTION OF THE INVENTION

The present invention provides a cosmetic composition, preferably in the form of a nail polish or other film-forming cosmetic composition. The composition has at least one primary film forming material and one or more high molecular weight polyurethane resins. Optionally, the cosmetic composition has at least one arylsulfonamide epoxy resin.

Preferably, the primary film former is a cellulose-based film former. More preferably, nitrocellulose is the primary film former. However, many cellulose-based materials, such as cellulose acetate, cellulose acetate butyrate, and ethyl cellulose, may be used either in combination with or as an alternative to nitrocellulose.

The cellulose-based primary film former is preferably present in an amount about 5 percent by weight (wt %) of the total weight of the composition to about 15 wt %. More preferably, the primary film former is about 7 wt % to about 12.5 wt % of the total weight of the composition.

An essential aspect of the present invention is the use of one or more high molecular weight polyurethane resins, which function as both film formers and plasticizers. Preferably the high molecular-weight polyurethane resins are polyether-type, high-molecular weight, polyurethane resins having an average molecular weight (MW) in the range of about 20,000 to about 80,000. The $t_g$ (glass transition temperature) of the preferred high-MW polyurethane resins is in the range of about −4° C. to about −20° C. and, more preferably, about −19° C. More preferred high-MW polyurethane resins have one of the following structures:

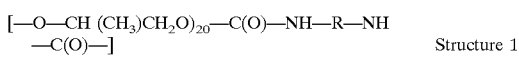  Structure 1

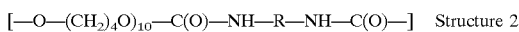  Structure 2 wherein R is an aliphatic moiety. Aliphatic polyurethane resins are preferred because they are more stable than aromatic polyurethane resins.

The high-MW polyurethane resins on a percent solids basis are preferably present in an amount about 2 wt % to about 15 wt %, and, more preferably, about 5 wt % to about 10 wt %.

Arylsulfonamide epoxy resins may also be included. For example, tosylamide epoxy resin may be added to the composition. Such arylsulfonamide epoxy resins enhance the aesthetics and gloss of the composition, but are not necessary to the functioning of the invention. When used, arylsulfonamide epoxy resins are preferably present in an amount about 1 wt % to about 15 wt % and, more preferably, about 3 wt % to about 8 wt %.

One or more plasticizers may also preferably be included in cosmetic compositions according to the present invention, but are not essential. When used, the plasticizer preferably is present in an amount about 1 wt % to about 9 wt % and, more preferably, about 2 wt % to about 5 wt %. Plasticizers useful in the present invention are those known in the art, including, without limitation, dibutyl phthalate (DBP) and other phthalates, tributyl acetyl citrate and other citrates, ethyl toluene sulfonamide (ethyl tosylamide), n-cyclohexyl para-toluene sulfonamide, glycerol and other glycols, glycol ethers, glycol esters, hydrogenated castor oil or epoxidized oils, polyesters, polybutylenes, low-MW aliphatic polyurethanes (about 2000 to about 5000 MW), toluene sulfonamide urea formaldehyde, γ-butyral lactone, n-butylphthalimide/isopropylphthalimide, ethylhexyl diphenyl phosphate, wool fat derivatives, chlorinated paraffins, glyceryl triacetate, camphor, sucrose acetate isobutyrate (SAIB), "slow" or high boiling solvents, low $t_g$ resins and polymers, and mixtures thereof. A more preferred cosmetic composition according to the present invention has ethyl toluene sulfonamide in an amount about 0.5 wt % to about 5 wt %. Conventional nail polish compositions have phthalates, such as DBP, as an essential component for imparting flexibility to the nail polish coating. It is highly surprising and unexpected that the nail polish compositions of the present invention can possess superior flexibility in the absence of phthalates, such as DBP.

The present invention may also have a solvent in an amount about 45 wt % to about 95 wt % and, more preferably, about 60 wt % to about 80 wt %. Examples of solvents useful in the present invention include, without limitation, alkylacetates, arylacetates, alcohols, ethers, ketones, alkanes, hydrocarbons, and water. Preferably, the cosmetic composition is anhydrous. More preferably, a cosmetic composition according to the present invention has butyl acetate in an amount about 20 wt % to about 40 wt %, ethyl acetate in an amount about 20 wt % to about 40 wt %, ethyl alcohol in an amount about 5 wt % to about 10 wt %, isopropanol in an amount about 1 wt % to about 10 wt % (more preferably about 3 wt % to about 6 wt %), and diacetone alcohol in an amount 0.5 wt % to about 5 wt %.

Additional ingredients that may be included in cosmetic compositions according to the present invention include stabilizing agents and pigments. When used, stabilizing agents, such as stearalkonium bentonite and stearalkonium hectorite, are present preferably in an amount about 0.1 wt % to about 3 wt % and, more preferably, about 0.75 wt % to about 1.5 wt %. In a most preferred embodiment for a nail polish, the stearalkonium bentonite and stearalkonium hecorite are present in about an equal amount. Furthermore, pigments are preferably present in an amount about 0.01 wt % to about 10 wt % and, more preferably, about 0.5 wt % to about 4 wt %.

Moreover, the present invention may include any other suitable ingredient, limited only by the purpose to which the cosmetic composition is intended. For example, a cosmetic composition according to the present invention may include: ultraviolet light absorbers, antioxidants, fragrances, moisturizers, medicaments, humectants, fillers, or mixtures thereof.

The following is an example of a cosmetic composition according to the present invention.

EXAMPLE 1

Cosmetic Composition

| Ingredient | Approximate wt % |
|---|---|
| solvent | 45–95 |
| primary film former | 5–15 |
| high-MW polyurethane resin | 2–15 |
| plasticizer | 1–9 |
| stabilizing agent | 0.1–3 |
| pigment | 0.01–10 |

The following is an example of a nail polish according to the present invention.

EXAMPLE 2

Nail Polish

| Ingredient | Approximate wt % |
|---|---|
| butyl acetate | 20–40 |
| ethyl acetate | 20–40 |
| ethyl alcohol | 5–10 |
| isopropanol | 1–10 |
| diacetone alcohol | 0.5–5 |
| nitrocellulose | 5–15 |
| high-MW polyurethane | 2–15 |
| tosylamide epoxy resin | 1–15 |
| ethyl tosylamide | 0.5–5 |
| stearalkonium hectorite | 0.05–1.5 |
| stearalkonium bentonite | 0.05–1.5 |
| pigments | 0.01–10 |

EXAMPLE 3

Nail polish composition A was formulated in accordance with Example 2. Nail polish composition B was similarly formulated, except composition B contained no high MW polyurethane. Compositions A and B were each cast onto a substrate, such as glass, dried for twenty four hours at ambient temperature to create a film, cut into sections approximately 1 inch by 4 inches by 0.001 inch thick, peeled from the substrate and placed onto an Instron apparatus to determine their mechanical properties. Composition A film and composition B film were each stressed or pulled by the Instron at the rate of 6 inches/minute. The displacement (inches) of each film was recorded at film fracture and is set forth below.

| | Composition A | Composition B |
|---|---|---|
| Displacement | 4.657 inches | 0.064 inches |

The present invention having been described with particular reference to the preferred forms thereof, it will be obvious that various changes and modifications may be made herein without departing from the spirit and scope of the invention as defined in the appended claims.

Wherefore we claim:

1. A cosmetic composition comprising:
    a cellulose-based film forming agent; and
    a polyurethane resin having a molecular weight about 20,000 to about 80,000, wherein said polyurethane resin has a Tg of about −4° C. to about −20° C. and said composition further comprises an arylsulfonamide epoxy resin.

2. The composition of claim 1, wherein said cellulose-based film forming agent is nitrocellulose.

3. The composition of claim 1, wherein said cellulose-based film forming agent is present in an amount about 5 wt % to about 15 wt % of the total weight of the composition.

4. The composition of claim 1, wherein said polyurethane resin has a $t_g$ of about −4° C. to about −20° C.

5. The composition of claim 1, wherein said polyurethane resin is selected from the group consisting of the general structures:

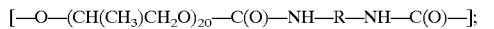

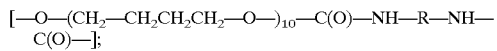

and combinations thereof, wherein R is an aliphatic moiety.

6. The composition of claim 1, wherein said polyurethane resin is present in an amount about 2 wt % to about 15 wt % of the total weight of the composition.

7. The composition of claim 1, further comprising a arylsulfonamide epoxy resin.

8. The composition of claim 7, wherein said arylsulfonamide epoxy resin is tosylamide epoxy resin.

9. The composition of claim 7, wherein said arylsulfonamide epoxy resin present in an amount about 1 wt % to about 15 wt % of the total weight of the composition.

10. The composition of claim 1, further comprising a solvent in an amount about 45 wt % to about 95 wt % of the total weight of the composition.

11. The composition of claim 1, further comprising a plasticizer.

12. The composition of claim 11, wherein said plasticizer is about 1 wt % to about 9 wt % of the total weight of the composition.

13. The composition of claim 1, further comprising at least one of a stabilizing agent and a pigment.

14. A cosmetic composition comprising:

a cellulose-based film forming agent present in an amount about 5 wt % to about 15% by weight of the total weight of the composition; and a polyurethane resin having a molecular weight about 20,000 to about 80,000 and present in an amount about 2 wt % to about 15 wt % by weight of the total weight of the composition, wherein said polyurethane resin has a Tg of about −4° C. to about −20° C. and said composition comprises an arylsulfonamide epoxy resin that is tosylamide epoxy resin.

15. The composition of claim 14, wherein said cellulose-based film forming agent is nitrocellulose.

16. The composition of claim 14, wherein said polyurethane resin has a $t_g$ of about −4° C. to about −20° C.

17. The composition of claim 14, wherein said polyurethane resin is selected from the group consisting of the general structures:

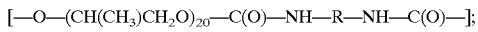

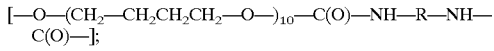

and combinations thereof, wherein R is a non-aromatic moiety.

18. The composition of claim 14, further comprising an arylsulfonamide epoxy resin in an amount about 1 wt % to about 15 wt % of the total weight of the composition.

19. The composition of claim 18, wherein said arylsulfonamide epoxy resin is tosylamide epoxy resin.

20. The composition of claim 18, further comprising a plasticizer present in an amount about 1 wt % to about 9 wt % of the total weight of the composition.

21. A method of imparting an improved flexible, durable and/or transfer resistant cosmetic coating to human nails comprising applying to the nails the composition of claim 1.

* * * * *